United States Patent
Kelly et al.

(10) Patent No.: US 8,521,554 B2
(45) Date of Patent: Aug. 27, 2013

(54) PRESENTING RELATED RESULTS DURING MEDICATION ADMINISTRATION DOCUMENTATION

(75) Inventors: Lisa Kelly, Overland Park, KS (US); Mary Gannon, Shawnee, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 558 days.

(21) Appl. No.: 12/351,420

(22) Filed: Jan. 9, 2009

(65) Prior Publication Data
US 2010/0179828 A1  Jul. 15, 2010

(51) Int. Cl.
*G06Q 50/00* (2012.01)
(52) U.S. Cl.
USPC .................................................. 705/2; 705/3
(58) Field of Classification Search
USPC ............................................................ 705/3
See application file for complete search history.

(56) References Cited

U.S. PATENT DOCUMENTS

| 2004/0010425 | A1* | 1/2004 | Wilkes et al. | 705/3 |
| 2008/0109260 | A1* | 5/2008 | Roof | 705/3 |
| 2008/0249804 | A1* | 10/2008 | Kim | 705/3 |
| 2009/0037224 | A1* | 2/2009 | Raduchel | 705/3 |
| 2009/0048868 | A1* | 2/2009 | Portnoy et al. | 705/2 |

* cited by examiner

*Primary Examiner* — Valerie Lubin
(74) *Attorney, Agent, or Firm* — Shook Hardy & Bacon LLP (57) ABSTRACT

Computerized methods and systems for receiving clinically-relevant discrete task assays related to a medication and for presenting results of the clinically-relevant discrete task assays during documentation of administration of the medication are provided. Medication identifiers are received and associated with discrete task assays, the results of which may be relevant to administration of the identified medication. Upon receipt of an indication that a clinician desires to administer the identified medication to a patient, the patient's electronic medical record is searched to determine if a result for any associated discrete task assays has been documented within a predefined time frame. If there is such a documented result, the result is presented in association with the location of the electronic medical record where administration of the medication is being documented.

15 Claims, 4 Drawing Sheets

PRESENTING RELATED RESULTS DURING MEDICATION ADMINISTRATION DOCUMENTATION

BACKGROUND

In clinical environments, administration of certain medications can be dependent on the results of discrete task assays, that is, certain laboratory tests, procedures, orderables, vital signs and the like, of the patient to whom a medication is to be administered. For instance, a patient having a low potassium level should not be administered the medication Digoxin, and a patient having a blood sugar level within a specified range should be administered only a certain amount of the medication Insulin. As such, such discrete task assays are often performed in conjunction with administration of a particular medication. However, oftentimes the same assays may have been performed by another clinician recently enough to still be considered acceptable for medication administration, unbeknownst to the clinician administering the medication, which can lead to repetitive testing, increased expense and inefficiency.

To avoid such repetition, the clinician administering the medication can browse an electronic medical record associated with the patient to determine if and when a result for the discrete task assay of interest was procured. However, this is a time consuming process and often requires navigation to multiple areas of the patient's electronic medical record where the particular result may be documented and stored.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter Embodiments of the present invention relate to systems and methods for receiving clinically-relevant discrete task assays (that is, certain laboratory tests, procedures, orderables, vital signs and the like) related to a medication and for presenting results of the clinically-relevant discrete task assays during documentation of administration of the medication. Medication identifiers are received and associated with discrete task assays, the results of which may be relevant to administration of the identified medication. Upon receipt of an indication that a clinician desires to administer the identified medication to a particular patient, the patient's electronic medical record is searched to determine if a result for any associated discrete task assays have been documented within a predefined time frame. If there is such a documented result, the result is presented in association with the location of the electronic medical record where administration of the medication is being documented. In this way, the clinician avoids having to search the patient's electronic medical record him or herself to determine if such a result exists or perform the discrete task assay at the time of administration of the medication.

Accordingly, in one embodiment, the present invention is directed to one or more computer-readable storage media having computer-executable instructions embodied thereon for performing a method, in a clinical computing environment, for presenting results of clinically-relevant discrete task assays. The method includes receiving an indication that a clinician desires to document administration of a particular medication to a patient, the indication being received in association with a medication administration documentation location of an electronic medical record associated with the patient; determining that there is at least one clinically-relevant discrete task assay, a result for which may be relevant to administration of the particular medication to the patient; determining that there is a result for the clinically-relevant discrete task assay stored in association with an electronic medical record associated with the patient; and presenting the result for the clinically-relevant discrete task assay in association with the medication administration documentation location of the patient's electronic medical record.

In another embodiment, the present invention is directed to a method, in a clinical computing environment, for receiving clinically-relevant discrete task assays related to a medication and for presenting results of the clinically-relevant discrete task assays during documentation of administration of the medication. The method includes receiving an identifier for the medication; receiving a clinically-relevant discrete task assay, a result for which may be relevant to administration of the medication; receiving an indication that a clinician desires to document administration of the medication to a particular patient, the indication being received in association with a medication administration documentation location of an electronic medical record associated with the particular patient; determining that there is a result for the clinically-relevant discrete task assay stored in association with the patient's electronic medical record; and presenting the result for the clinically-relevant discrete task assay in association with the medication administration documentation location of the particular patient's electronic medical record.

In yet another embodiment, the present invention is directed to a system having a processor and one or more computer-readable storage media for performing a method in a clinical computing environment for receiving clinically-relevant discrete task assays related to a medication and for presenting results of the clinically-relevant discrete task assays during documentation of administration of the medication. The system includes a medication identifier receiving component, a clinically-relevant discrete task assay receiving component, a medication administration indication receiving component, a search component, and a presentation component. The medication identifier receiving component is configured for receiving an identifier for the medication. The clinically-relevant discrete task assay receiving component is configured for receiving at least one clinically-relevant discrete task assay, a result for which may be relevant to administration of the medication. The medication administration indication receiving component is configured for receiving an indication that a clinician desires to document administration of the medication to a particular patient, the indication being received in association with a medication administration documentation location of an electronic medical record associated with the particular patient. The search component is configured for determining that there is at least one clinically-relevant discrete task assay, a result for which may be relevant to administration of the medication to the particular patient, and for determining that there is a result for the clinically-relevant discrete task assay stored in association with the electronic medical record associated with the particular patient. The presentation component is configured for presenting the result for the clinically-relevant discrete task assay in association with the medication administration documentation location of the electronic medical record associated with the particular patient. If desired, the system may further include an action receiving component configured for receiving an acknowledgement of the result for the clinically-relevant discrete task assay and/or documentation of a second result for the clinically-relevant discrete task assay in association with the medication administration documentation location of the particular patient's electronic medical record.

BRIEF DESCRIPTION OF THE DRAWINGS

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention provide computerized methods and systems for receiving clinically-relevant discrete task assays (DTAs) related to a medication administration and for presenting results of the clinically-relevant DTAs during documentation of administration of the medication. Medication identifiers are received and associated with DTAs, the results of which may be relevant to administration of the identified medication. Upon receipt of an indication that a clinician desires to administer the identified medication to a particular patient, the patient's electronic medical record (EMR) is searched to determine if a result for any associated DTAs has been documented within a predefined time frame. If there is such a documented result, the result is presented in association with the location of the EMR where administration of the medication is being documented. In this way, the clinician avoids having to search the patient's EMR him or herself to determine if such a result exists or perform the DTA at the time of administration of the medication. An exemplary operating environment for embodiments of the present invention is described below.

Figure 1:
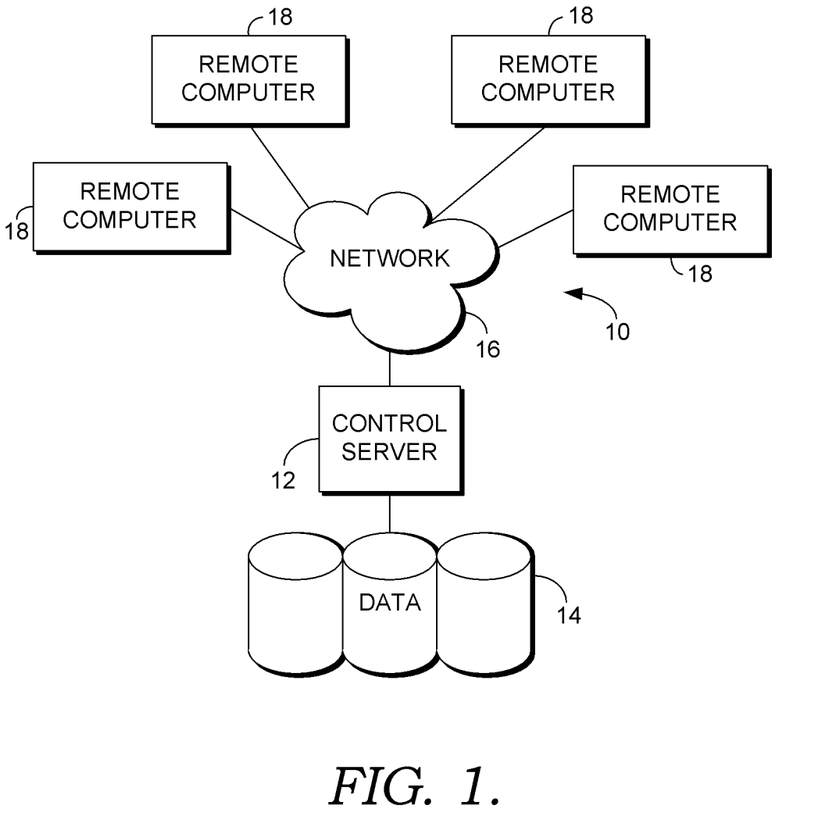
FIG. 1 is a block diagram of an exemplary computing environment suitable for use in implementing the present invention.

Referring to the drawings in general, and initially to FIG. 1 in particular, an exemplary computing system environment, for instance, a medical information computing system, on which embodiments of the present invention may be implemented is illustrated and designated generally as reference numeral 10. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 10 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 10 includes a general purpose computing device in the form of a server 12. Components of the server 12 may include, without limitation, a processing unit, internal system memory, and a suitable system bus for coupling various system components, including database cluster 14, with the server 12. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 12 typically includes, or has access to, a variety of computer readable media, for instance, database cluster 14. Computer readable media can be any available media that may be accessed by server 12, and includes volatile and nonvolatile media, as well as removable and non-removable media. By way of example, and not limitation, computer readable media may comprise computer storage media. Computer storage media may include, without limitation, volatile and nonvolatile media, as well as removable and non-removable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 12. Combinations of any of the above also may be included within the scope of computer readable media.

The computer storage media discussed above and illustrated in FIG. 1, including database cluster 14, provide storage of computer readable instructions, data structures, program modules, and other data for the server 12.

The server 12 may operate in a computer network 16 using logical connections to one or more remote computers 18. Remote computers 18 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 18 may also be physically located in non-traditional medical care environments so that the entire health care community may be capable of integration on the network. The remote computers 18 may be personal computers, servers, routers, network PCs, peer devices, other common network nodes, or the like, and may include some or all of the elements described above in relation to the server 12. The devices can be personal digital assistants or other like devices.

Exemplary computer networks 16 may include, without limitation, local area networks (LANs) and/or wide area networks (WANs). Such networking environments are commonplace in offices, enterprise-wide computer networks, intranets, and the Internet. When utilized in a WAN networking environment, the server 12 may include a modem or other means for establishing communications over the WAN, such as the Internet. In a networked environment, program modules or portions thereof may be stored in the server 12, in the database cluster 14, or on any of the remote computers 18. For example, and not by way of limitation, various application programs may reside on the memory associated with any one or more of the remote computers 18. It will be appreciated by those of ordinary skill in the art that the network connections shown are exemplary and other means of establishing a communications link between the computers (e.g., server 12 and remote computers 18) may be utilized.

In operation, a user may enter commands and information into the server 12 or convey the commands and information to the server 12 via one or more of the remote computers 18 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 12. In addition to a monitor, the server 12 and/or remote computers 18 may include other peripheral output devices, such as speakers and a printer.

Although many other internal components of the server 12 and the remote computers 18 are not shown, those of ordinary skill in the art will appreciate that such components and their interconnection are well known. Accordingly, additional details concerning the internal construction of the server 12 and the remote computers 18 are not further disclosed herein.

Although methods and systems of embodiments of the present invention are described as being implemented in a WINDOWS operating system, operating in conjunction with an Internet-based system, one of ordinary skill in the art will recognize that the described methods and systems can be implemented in any system supporting the receipt and processing of healthcare-related orders, particularly, molecular diagnostic orders. As contemplated by the language above, the methods and systems of embodiments of the present invention may also be implemented on a stand-alone desktop, personal computer, or any other computing device used in a healthcare environment or any of a number of other locations.

Figure 2:
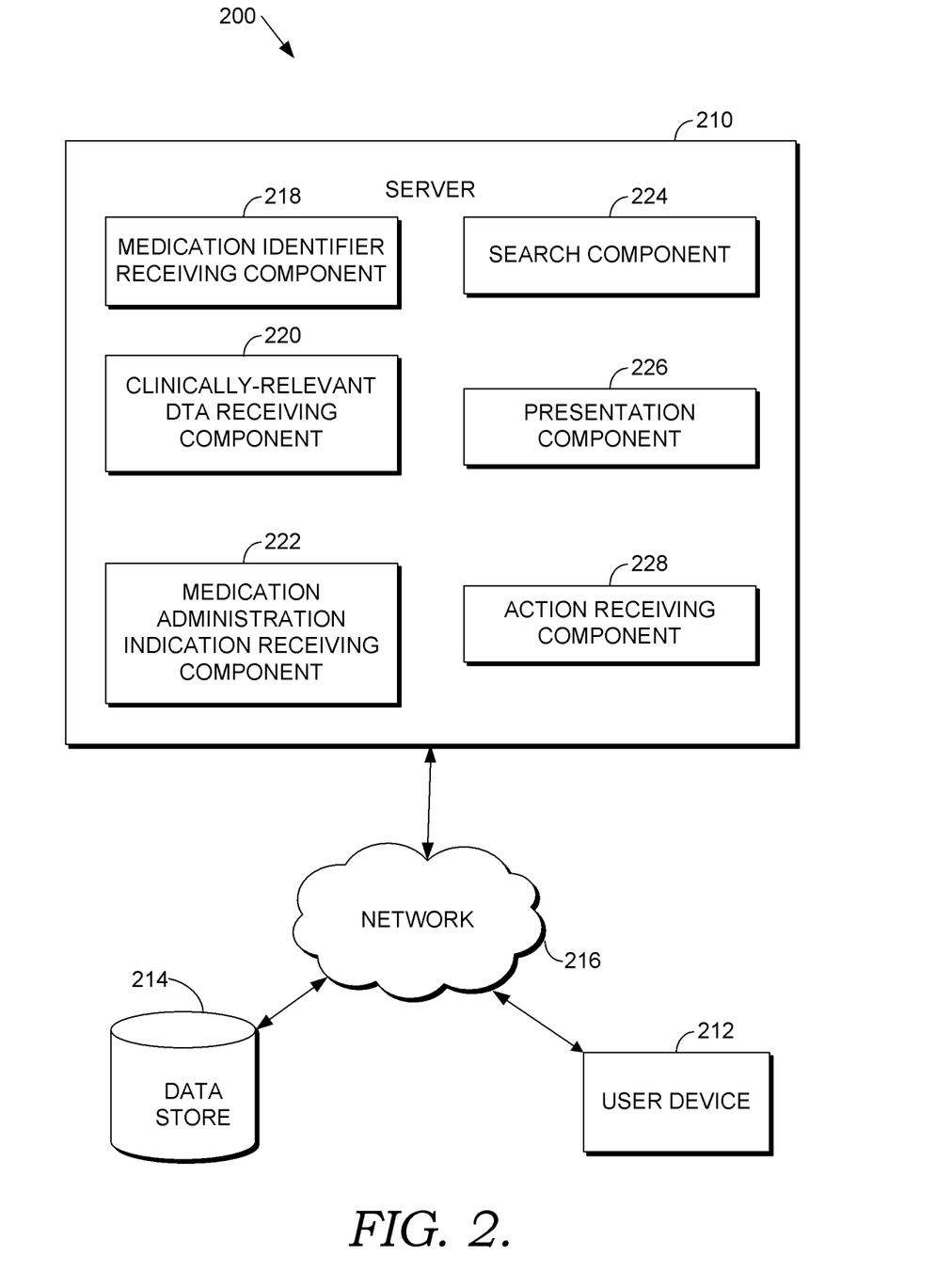
FIG. 2 is a block diagram of an exemplary computing system suitable for implementing embodiments of the present invention.

As previously mentioned, embodiments of the present invention relate to computerized methods and systems for receiving clinically-relevant discrete task assays (that is, certain laboratory tests, procedures, orderables, vital signs and the like) related to a medication and for presenting results of the clinically-relevant discrete task assays during documentation of administration of the medication. With reference to FIG. 2, an exemplary computing system suitable for implementing embodiments of the present invention is illustrated and designated generally as reference numeral 200. System 200 includes a server 210, a user device 212, and a data store 214, all in communication with one another through a network 216. The network 216 may include, without limitation, one or more local area networks (LANs) and/or wide area networks (WANs). Such networking environments are commonplace in offices, enterprise-wide computer networks, intranets, and the Internet. Accordingly, the network 216 is not further described herein.

The data store 214 is configured to store information, for instance, associated with discrete task assays (DTAs); a plurality of patient's electronic medical records (EMRs), including DTA results stored in association therewith; and medications and associated medication identifiers. (The terms "individual", "person", and "patient" are used interchangeably herein and are not meant to limit the nature of the referenced individual in any way. Rather the methods and systems described herein are equally applicable, for instance, in a veterinary setting. Further, use of the term "patient" is not meant to imply any particular relationship between the individual and those inputting, ordering and/or individualizing the clinical order.) In various embodiments, such information may include, without limitation, a plurality of medication identifiers, each associated with a particular medication; one or more DTAs, the results for which may be relevant to administration of one or more medications identified by the plurality of medication identifiers; EMRs associated with a plurality of patients, each EMR having a plurality of documents and/or documentation locations associated therewith and results of clinically-relevant DTAs, and the like. In embodiments, the data store 214 is configured to be searchable for one or more DTAs associated with particular medications, and/or results of such DTAs within the EMRs of patients to whom administration of the particular medications is desired. It will be understood and appreciated by those of ordinary skill in the art that the information stored in the data store 214 may be configurable and may include any information relevant to patients' EMRs, medications, and/or DTAs and DTA results associated therewith. The content and volume of such information are not intended to limit the scope of embodiments of the present invention in any way. Further, though illustrated as a single, independent component, the data store 214 may, in fact, be a plurality of data stores, for instance, a database cluster (e.g., database cluster 14 of FIG. 1), portions of which may reside on the server 210, the user device 212, another external computing device (not shown) and/or any combination thereof.

The server 210 includes various components and is configured to operate utilizing at least a portion of the information stored in the data store 214. The illustrated server 210 includes a medication identifier receiving component 218, a clinically-relevant DTA receiving component 220, a medication administration indication receiving component 222, a search component 224, a presentation component 226, and an action receiving component 228. It will be understood and appreciated by those of ordinary skill in the art that other components not shown may also be included with the system 200. Further, additional components not shown may also be included within any of the server 210, the user device 212, the data store 214, and/or another external computing device (not shown). Any and all such variations are contemplated to be within the scope of embodiments hereof.

The medication identifier receiving component 218 is configured to receive an identifier associated with a particular medication. Received medication identifiers indicate that a clinician or other user desires to identify one or more DTAs, a result for which may be clinically-relevant to administration of the medication associated therewith.

The clinically-relevant DTA receiving component 220 is configured to receive at least one clinically-relevant discrete task assay, a result for which may be relevant to administration of a particular identified medication to a patient. In practice, a user generally inputs a medication identifier at a user device 212, the medication identifier is received by the medication identifier receiving component 218 (via network 216), the user inputs at least one clinically-relevant DTA at the user device 212, the at least one clinically-relevant DTA is received by the clinically-relevant DTA receiving component (via network 216) and the received medication identifier and the at least one clinically-relevant DTA are associated with one another, for instance, utilizing either the medication identifier receiving component 218, the clinically-relevant DTA receiving component 220, or another associating component (not shown) of server 210. The association of the received medication identifier and the received at least one DTA is subsequently stored, for instance, in association with data store 214. Once associated with one another, the at least one clinically-relevant DTA may be retrieved and presented to a user, and/or a result for the at least one clinically-relevant DTA may be retrieved and presented to a user, upon the user indicating administration of the medication identified by the associated medication identifier is desired, as more fully described below. It will be understood by those of ordinary skill in the art that user input of medication identifiers and/or associated clinically-relevant DTAs may be via free text entry, selection of a predefined selectable option, or the like.

The medication administration indication receiving component 222 is configured to receive an indication that a clinician desires to document administration of a particular medication to a patient. Such indication is generally received in association with a medication administration documentation location of an electronic medical record (EMR) associated with the particular patient. That is, in practice, a clinician or other user having access to the patient's EMR, accesses the medication administration documentation location thereof, for instance, utilizing user device 212, and inputs a desire to administer a particular medication to the patient associated with the accessed EMR. Such desire is generally evidenced by input of a medication identifier associated with the medication for which administration is desired, e.g., via free text entry, selection of predefined selectable options, or the like. The input desire is received (via network 216) by the medication administration indication receiving component 222.

Upon receipt of a desire to administer a particular medication to a particular patient, the search component 224 is configured to search one or more data stores, e.g., data store 214, to determine if there is at least one clinically-relevant discrete task assay associated therewith, a result for which may be relevant to administration of the medication. That is, the search component is configured to search one or more data stores (for instance, data store 214) to determine if a medication identifier input by a user and received by medication administration indication receiving component 222 is associated with one or more DTAs, a result for which may be clinically-relevant to administration of the medication identified thereby. If it is determined that there is not a clinically-relevant DTA, a result for which may be clinically-relevant to administration of the medication, a message indicating such may be presented to the user (for instance, utilizing presentation component 226, as more fully described below). Alternatively, the system 200 may not display a message of any kind upon such determination, the absence of any message itself indicating there is not a clinically-relevant DTA associated with the medication identified by the input medication identifier. Any and all such variations, and any combination thereof, are contemplated to be within the scope of embodiments of the present invention.

If, however, it is determined that there is at least one clinically-relevant DTA, a result for which may be clinically-relevant to administration of a particular medication, the search component 224 is further configured to search the patient's EMR to determine if there is a result for the clinically-relevant DTA stored in association therewith. The patient's EMR is typically comprised of a plurality of documents and/or information documentation locations (for instance, fillable forms). Thus, the search component 224 is configured to search each of the documents and information documentation locations comprising the patient's EMR for a result for the clinically-relevant DTA associated with the medication for which administration is indicated to be desired.

In embodiments, only results for clinically-relevant DTAs that were procured, documented and/or stored within a particular predefined time frame are of interest to administration of a particular medication. For instance, only results procured within the thirty minutes prior to receipt of the indication of a desire to administer the particular medication may be of interest at the time of medication administration. Thus, the search component 224 may be further configured to filter determined results for a clinically-relevant DTA according to one or more predefined time frame filters. Further, in embodiments, only the most recently procured, documented and/or stored result of a clinically-relevant DTA may be of interest at the time of medication administration. Thus, the search component 224 may be further configured to filter a plurality of determined results for a clinically-relevant DTA such that only the most recent result therefore is identified. Any and all such variations, and any combination thereof, are contemplated to be within the scope of embodiments of the present invention.

If it is determined that there is not a result for the associated clinically-relevant DTA stored in association with the patient's EMR, a message indicating such may be presented to the user (for instance, utilizing presentation component 226, as more fully described below). Alternatively, the system 200 may not display a message of any kind upon such determination, the absence of any message itself indicating there is not a result for any clinically-relevant DTA associated with the medication identified by the input medication identifier.

Any and all such variations, and any combination thereof, are contemplated to be within the scope of embodiments of the present invention.

The presentation component 226 is configured to present one or more results for an identified clinically-relevant DTA in association with the medication administration documentation location of the EMR associated with the particular patient to whom medication administration has been indicated to be desired. That is, the presentation component 226 is configured to receive any results stored in association with the particular patient's EMR and identified by the search component 224, and present those results in association with the medication administration documentation location of the patient's EMR, i.e., in association with the same location within the patient's EMR that the user had input an indication of a desire to administer the particular medication to the patient. In this way, the user can immediately view, without having to manually navigate through the patient's EMR, any DTA results stored in association with the patient's EMR that may be relevant to administration of the desired medication. In embodiments, the presentation component 226 is further configured to present one or more messages indicating that no clinically-relevant DTAs are associated with the medication identified by the input medication identifier, no results for an associated clinically-relevant DTA are stored in association with the patient's EMR, or the like.

In embodiments, the presented result may include a selectable link, selection of which navigates the user to the location(s) within the patient's EMR where the presented DTA result is stored. Further, in embodiments, if it is determined by the search component 224 that a plurality of results for a clinically-relevant DTA is stored in association with the patient's EMR, only a single result, generally the most recent result, is presented to the user (utilizing presentation component 226). However, the fact that multiple results to the clinically-relevant DTA are stored in association with the patient's EMR may be evidenced by a selectable link being presented to the user in association with the presented result. Selection of the selectable link may then navigate the user to the location(s) within the patient's EMR where the DTA results are stored. Such multiple result display may be set to either honor or not honor the predefined time frame associated with the initially displayed clinically-relevant DTA results, as desired. Further, trending of DTA results may be presented, if desired. Any and all such variations, and any combination thereof, are contemplated to be within the scope of embodiments of the present invention.

In some embodiments, a presented DTA result may be presented as view-only for the user. Thus, the user is only able to view the result and take no action with respect thereto. In other embodiments, an action with respect to a presented DTA result may be required of the user. In this regard, the action receiving component 228 is configured to receive an action from the user with respect to a presented DTA result. Such actions may include, without limitation, an acknowledgement of the result for the clinically-relevant DTA and/or documentation of a second result for the clinically-relevant DTA, any such action being received in association with the medication administration documentation location of the electronic medical record associated with the particular patient. Acknowledgement of the result indicates that the user has reviewed the presented result for the medication administration and wishes to associate the result to the specific medication administration being documented. Such acknowledgement may be stored in association with the medication administration task being documented in the patient's EMR. If, however, the user desires or the system requires the user to document a result taken contemporaneously with medication administration, the user may be able or required to document such result. In embodiments, such acknowledgement and/or documentation may be required before documentation of medication administration is permitted.

In embodiments, the ability to acknowledge or document a DTA result honors existing privileges for medication documentation. Thus, if the user has the privilege to document administration of the medication, he or she also has the privilege to acknowledge and/or document a clinically-relevant DTA. Further, in embodiments, retrospective documentation is permitted. That is, if the medication administration date and/or time is altered, a clinically-relevant DTA result based on the newly input time will be determined and, if appropriate, presented to the user. If this result is acknowledged and/or a new result for the DTA is documented, such will become associated with administration of the medication in the patient's EMR.

Figure 3:
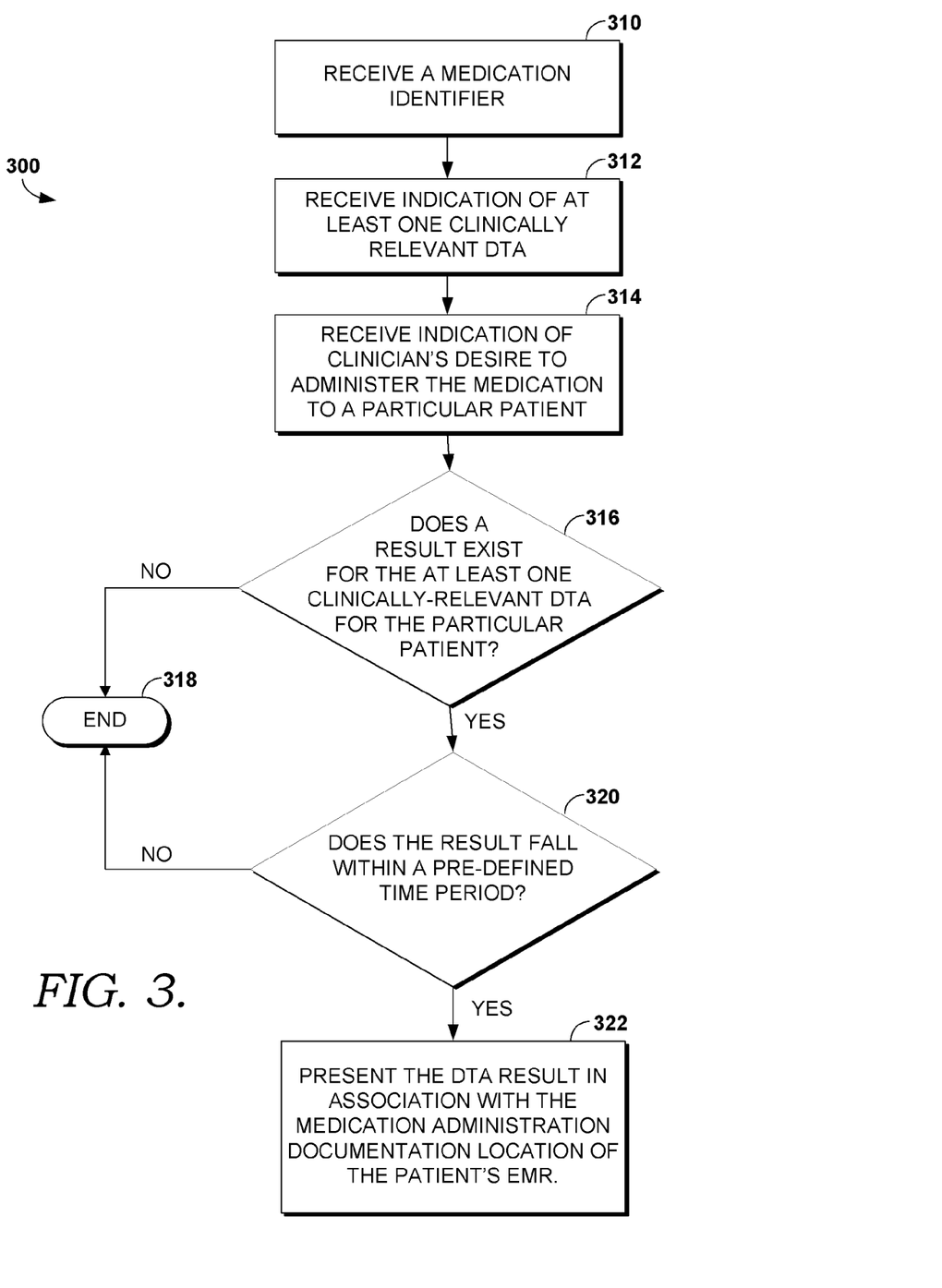
FIG. 3 is a flow diagram showing a method for receiving clinically-relevant discrete task assays (DTAs) related to a medication and for presenting results of the clinically-relevant DTAs during documentation of administration of the medication, in accordance with an embodiment of the present invention.

Turning now to FIG. 3, a flow diagram showing a method for receiving clinically-relevant discrete task assays (DTAs) related to a medication and for presenting results of the clinically-relevant DTAs during documentation of administration of the medication, in accordance with an embodiment of the present invention, is illustrated and designated generally as reference numeral 300. Method 300 may be implemented in the above-described exemplary computing system environment (FIG. 2), and, by way of example only, may be utilized by a clinician to view DTA results related to administration of a particular medication to a patient while documenting administration thereof.

Initially, as indicated at block 310, an identifier for a particular medication is received, for instance, utilizing medication identifier receiving component 218 of FIG. 2. At block 312, an indication is received of at least one clinically-relevant discrete task assay, a result for which may be relevant to administration of the medication identified by the received medication identifier. Such indication may be received, e.g. utilizing clinically-relevant discrete task assay receiving component 220 of FIG. 2.

At block 314, an indication that a clinician desires to document administration of the identified medication to a particular patient is received, for instance, utilizing medication administration indication receiving component 222 of FIG. 2. The indication is received in association with a medication administration documentation location of an electronic medical record associated with the particular patient.

At block 316, it is determined (e.g., utilizing search component 224 of FIG. 2) whether or not there is a result for the clinically-relevant discrete task assay stored in association with the patient's electronic medical record. If it is determined that no result for the clinically-relevant discrete task assay is stored in association with the patient's electronic medical record, the method ends, as indicated at block 318. If, however, it is determined at block 316 that at least one result for the clinically-relevant discrete task assay is stored in association with the patient's electronic medical record, it is determined at block 320 if the result was procured, documented and/or stored within a predefined time period. If the result was not documented and/or stored within the predefined time period, the method ends, as indicated at block 318.

If, however, it is determined that the result was procured, documented and/or stored within the predefined time period, the result for the clinically-relevant discrete task assay is presented (e.g. utilizing presentation component 226 of FIG. 2) in association with the medication administration documentation location of the electronic medical record associated with the particular patient. This is indicated at block 322.

Figure 4:
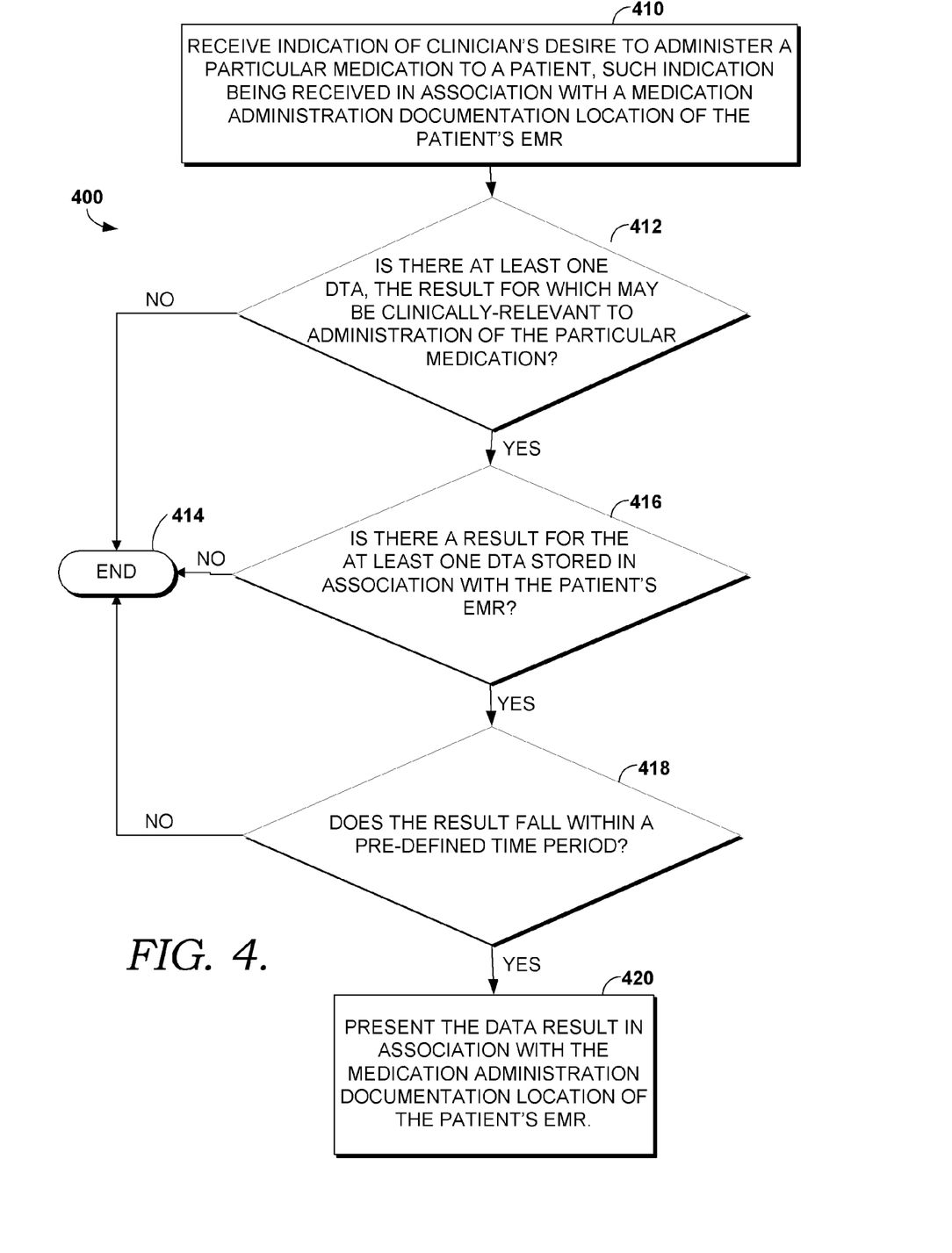
FIG. 4 is a flow diagram showing a method for presenting results of clinically-relevant DTAs during documentation of administration of a particular medication, in accordance with an embodiment of the present invention.

Turning now to FIG. 4, a flow diagram showing a method for presenting results of clinically-relevant DTAs during documentation of administration of a particular medication, in accordance with an embodiment of the present invention, is illustrated and designated generally as reference numeral 400. Method 400 may be implemented in the above-described exemplary computing system environment (FIG. 2), and, by way of example only, may be utilized by a clinician to view DTA results related to administration of a particular medication to a patient while documenting administration thereof.

Initially, as indicated at block 410, an indication that a clinician desires to document administration of a particular medication to a patient is received, for instance, utilizing medication administration indication receiving component 222 of FIG. 2. The indication is received in association with a medication administration documentation location of an electronic medical record associated with the patient. As indicated at block 412, it is next determined (e.g., utilizing search component 224 of FIG. 2) if there is at least one clinically-relevant discrete task assay, a result for which may be relevant to administration of the particular medication to the patient. If it is determined that there is not at least one clinically-relevant discrete task assay, a result for which may be relevant to administration of the particular medication to the patient, the method ends, as indicated at block 414.

If, however, it is determined that there is at least one clinically-relevant discrete task assay, a result for which may be relevant to administration of the particular medication to the patient, it is next determined whether or not there is a result for the at least one clinically-relevant discrete task assay stored in association with an electronic medical record associated with the patient. If it is determined that there is not a result for the at least one clinically-relevant discrete task assay stored in association with the patient's electronic medical record, the method ends, as indicated at block 414.

If, however, it is determined that there is a result for the at least one clinically-relevant discrete task assay stored in association with the patient's electronic medical record, it is next determined whether or not the result was procured, documented and/or stored in association with the patient's electronic medical record within a predefined time period. If it is determined that the result was not procured, documented and/or stored in association with the patient's electronic medical record within the predefined time period, the method ends, as indicated at block 414. In embodiments (not shown), a message indicating that no acknowledgeable result had been documented within the predefined time period may be presented within the medication administration window.

If, however, it is determined that the result was procured, documented and/or stored in association with the patient's electronic medical record within the predefined time period, the result is presented (e.g., utilizing presentation component 226 of FIG. 2) in association with the medication administration documentation location of the patient's electronic medical record.

As can be understood, embodiments of the present invention provide computerized methods and systems for receiving clinically-relevant discrete task assays related to a medication and for presenting results of the clinically-relevant discrete task assays during documentation of administration of the medication. Medication identifiers are received and associated with discrete task assays, the results of which may be relevant to administration of the identified medication. Upon receipt of an indication that a clinician desires to administer the identified medication to a particular patient, the patient's electronic medical record is searched to determine if a result for any associated discrete task assays have been documented within a predefined time frame. If there is such a documented result, the result is presented in association with the location of the electronic medical record where administration of the medication is being documented. In this way, the clinician avoids having to search the patient's electronic medical record him or herself to determine if such a result exists or perform the discrete task assay at the time of administration of the medication.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated and within the scope of the claims.

What is claimed is:

1. One or more computer-readable storage media having computer-executable instructions embodied thereon for performing a method in a clinical computing environment for presenting results of clinically-relevant discrete task assays, the method comprising:

generating a medication identifier/discrete task assay electronic data store, wherein generating the medication identifier/discrete task assay electronic data store comprises:

(1) receiving a medication identifier associated with a first medication;

(2) receiving at least one discrete task assay that is independent of patient data, the discrete task assay being clinically relevant to the first medication;

(3) associating the medication identifier with the at least one discrete task assay;

receiving an indication that a clinician desires to document administration of the first medication to a patient, the indication being received in association with a medication administration documentation location of an electronic medical record data store associated with the patient;

incident to receiving the indication that the clinician desires to document administration of the first medication to the patient, automatically searching, using a search component, the medication identifier/discrete task assay electronic data store to determine the at least one clinically-relevant discrete task assay associated with the medication identifier of the first medication;

incident to determining the at least one clinically-relevant discrete task assay associated with the medication identifier of the first medication, automatically searching, using the search component, the electronic medical record data store associated with the patient to determine that the patient's electronic medical record data store has a patient result corresponding to the at least one clinically-relevant discrete task assay;

determining that the patient result corresponding to the at least one clinically-relevant discrete task assay was generated within a predefined time frame prior to receiving the indication that the clinician desires to document administration of the first medication to the patient; and presenting the patient result corresponding to the at least one clinically-relevant discrete task assay in association with the medication administration documentation location of the electronic medical record data store associated with the patient.

2. The one or more computer-readable storage media of claim 1,
wherein searching, using the search component, the patient's electronic medical record data store to determine that the patient's electronic medical record data store has a patient result corresponding to the at least one clinically-relevant discrete task assay comprises determining that there are a plurality of patient results corresponding to the at least one clinically-relevant discrete task assay that were generated within the predefined time frame,
and wherein presenting the patient result corresponding to the at least one clinically-relevant discrete task assay comprises presenting a most recent patient result corresponding to the at least one clinically-relevant discrete task assay in association with the medication administration documentation location of the patient's electronic medical record data store.

3. The one or more computer-readable storage media of claim 1, wherein the method further comprises permitting the clinician to only view the presented patient result.

4. The one or more computer-readable storage media of claim 1, wherein the method further comprises receiving acknowledgement of the presented patient result in association with the medication administration documentation location of the patient's electronic medical record data store.

5. The one or more computer-readable storage media of claim 1, wherein the method further comprises receiving documentation of a second patient result corresponding to the at least one clinically-relevant discrete task assay in association with the medication administration documentation location of the electronic medical record data store.

6. The one or more computer-readable storage media of claim 1, wherein the method further comprises requiring the clinician to either acknowledge the presented patient result or document a second patient result corresponding to the at least one clinically-relevant discrete task assay in association with the medication administration documentation location of the patient's electronic medical record data store.

7. The one or more computer-readable storage media of claim 1, wherein presenting the patient result corresponding to the at least one clinically-relevant discrete task assay in association with the medication administration documentation location of the patient's electronic medical record data store comprises presenting a selectable link, selection of which navigates the clinician to a location of the patient's electronic medical record data store where the presented patient result was documented and/or stored.

8. The one or more computer-readable storage media of claim 1,
wherein searching, using the search component, the patient's electronic medical record data store to determine that the patient's electronic medical record data store has a patient result corresponding to the at least one clinically-relevant discrete task assay comprises determining that there are a plurality of patient results corresponding to the at least one clinically-relevant discrete task assay that were generated within the predefined time frame,
and wherein presenting the patient result corresponding to the at least one clinically-relevant discrete task assay comprises presenting a most recent patient result of the plurality of patient results and a selectable link, selection of which initiates display of each of the plurality of patient results.

9. A method in a clinical computing environment for receiving clinically-relevant discrete task assays related to a medication and for presenting results of the clinically-relevant discrete task assays during documentation of administration of the medication, the method comprising:
storing computer useable instructions on a computer storage media; and
executing the computer useable instructions by one or more computing devices, causing the one or more computing devices to:
(1) generate a first electronic data store by
a) receiving an identifier for the medication;
b) receiving a clinically-relevant discrete task assay that is independent of patient data, the clinically-relevant discrete task assay being relevant to administration of the medication;
c) associating the identifier for the medication and the clinically-relevant discrete task assay;
(2) receive an indication that a clinician desires to document administration of the medication to a particular patient, the indication being received in association with a medication administration documentation location of an electronic medical record data store associated with the particular patient;
(3) incident to receiving the indication, automatically search, using a search component, the first electronic data store to identify the clinically-relevant discrete task assay stored in association with the identifier for the medication;
(4) incident to identifying the clinically-relevant discrete task assay, automatically search, using the search component, the particular patient's electronic medical record data store to determine that there is a plurality of patient results corresponding to the clinically-relevant discrete task assay, wherein the plurality of patient results were generated prior to receiving the indication that the clinician desires to document the administration of the medication to the particular patient;
(5) determine a most recent patient result of the plurality of patient results, the most recent patient result being generated within a predefined time range of receiving the indication that the clinician desires to document administration of the medication to the particular patient;
(6) present the most recent patient result of the plurality of results corresponding to the clinically-relevant discrete task assay in association with the medication administration documentation location of the electronic medical record data store associated with the particular patient;
(7) present a selectable link in association with the most recent patient result of the plurality of patient results;
(8) receive a selection of the selectable link; and
(9) present a remainder of the plurality of patient results corresponding to the clinically-relevant discrete task assay in association with the medication administration documentation location of the electronic medical record data store associated with the particular patient.

10. The method of claim 9, wherein executing the computer useable instructions further causes the one or more computing devices to permit the clinician to only view the most recent patient result.

11. The method of claim 9, wherein executing the computer useable instructions further causes the one or more computing devices to receive acknowledgement of the most recent patient result in association with the medication administration documentation location of the electronic medical record data store associated with the particular patient.

12. The method of claim 9, wherein executing the computer useable instructions further causes the one or more computing devices to receive documentation of a second patient result corresponding to the clinically-relevant discrete task assay in association with the medication administration documentation location of the electronic medical record data store.

13. The method of claim 9, wherein executing the computer useable instructions further causes the one or more computing devices to require the clinician to either acknowledge the presented patient result or document a second patient result corresponding to the clinically-relevant discrete task assay in association with the medication administration documentation location of the electronic medical record data store associated with the particular patient.

14. A system for performing a method in a clinical computing environment for receiving clinically-relevant discrete task assays related to a medication and for presenting results of the clinically-relevant discrete task assays during documentation of administration of the medication, the system comprising:

a processor and one or more computer-readable storage media;

a medication identifier receiving component for receiving an identifier for the medication;

a clinically-relevant discrete task assay receiving component for receiving at least one clinically-relevant discrete task assay independent of patient data and associating the at least one clinically-relevant discrete task assay with the medication identifier, the association of the at least one clinically-relevant discrete task assay and the medication identifier being stored in association with a medication identifier/discrete task assay electronic data store;

a medication administration indication receiving component for receiving an indication that a clinician desires to document administration of the medication to a particular patient, the indication being received in association with a medication administration documentation location of an electronic medical record data store associated with the particular patient;

a search component for:
 (1) automatically searching the medication identifier/discrete task assay electronic data store incident to receiving the indication that the clinician desires to document administration of the medication to the particular patient, the search component searching the medication identifier/discrete task assay electronic data store to determine the at least one clinically-relevant discrete task assay associated with the medication identifier;
 (2) incident to determining the at least one clinically-relevant discrete task assay associated with the medication identifier, searching the patient's electronic medical record data store to determine that there is a patient corresponding to the at least one clinically-relevant discrete task assay, wherein the patient result was generated within a predefined time frame prior to the medication administration indication receiving component receiving the indication that the clinician desires to document administration of the medication to the particular patient; and a presentation component for presenting the patient result corresponding to the at least one clinically-relevant discrete task assay in association with the medication administration documentation location of the electronic medical record data store associated with the particular patient.

15. The system of claim 14, further comprising an action receiving component for receiving an acknowledgement of the patient result corresponding to the at least one clinically-relevant discrete task assay and/or documentation of a second patient result corresponding to the clinically-relevant discrete task assay in association with the medication administration documentation location of the electronic medical record data store associated with the particular patient.

* * * * *